(12) United States Patent
Hunter

(10) Patent No.: US 10,768,113 B2
(45) Date of Patent: Sep. 8, 2020

(54) DEVICE FOR READING AN IVD ASSAY

(71) Applicant: Lumos Diagnostics IP PTY LTD, Box Hill, Victoria (AU)

(72) Inventor: William Samuel Hunter, Bellbrae (AU)

(73) Assignee: Lumos Diagnostics IP PTY LTD, Victoria (AU)

( * ) Notice: Subject to any disclaimer, the term of this patent is extended or adjusted under 35 U.S.C. 154(b) by 0 days.

(21) Appl. No.: 16/507,566

(22) Filed: Jul. 10, 2019

(65) Prior Publication Data

US 2020/0011801 A1 Jan. 9, 2020

Related U.S. Application Data

(63) Continuation of application No. 15/755,999, filed as application No. PCT/AU2016/050965 on Oct. 14, 2016, now Pat. No. 10,379,049.

(30) Foreign Application Priority Data

Oct. 15, 2015 (AU) ................. 2015904206

(51) Int. Cl.
*G01N 33/53* (2006.01)
*G01N 21/64* (2006.01)
(Continued)

(52) U.S. Cl.
CPC ....... *G01N 21/6456* (2013.01); *G01N 21/274* (2013.01); *G01N 21/8483* (2013.01); *G01N 33/53* (2013.01)

(58) Field of Classification Search
CPC ............. G01N 21/274; G01N 21/8483; G01N 21/6456; G01N 33/53; G01N 33/533
See application file for complete search history.

(56) References Cited

U.S. PATENT DOCUMENTS 4,626,684 A 12/1986 Landa
2003/0040031 A1* 2/2003 Kim ................ B01L 3/5025
435/29
(Continued)

FOREIGN PATENT DOCUMENTS

CN 103852879 6/2014
WO WO 2002/008762 1/2002
(Continued)

OTHER PUBLICATIONS

EPO Application No. 16854649.7, Communication pursuant to Rule 164(1) EPC, dated Mar. 29, 2019, 19 pages.
(Continued)

*Primary Examiner* — David P Porta
*Assistant Examiner* — Fani Boosalis
(74) *Attorney, Agent, or Firm* — Edward J. Baba; Bozicevic, Field & Francis LLP

(57) ABSTRACT

Embodiments generally relate to a system for reading fluorescent-labelled diagnostic assays for in-vitro diagnostic applications. The system comprises a receiving member adapted to receive a fluorescent-labelled diagnostic assay cartridge carrying a fluorescent-labelled diagnostic assay; at least one excitation module configured to illuminate the diagnostic assay, when the diagnostic assay cartridge is placed in the receiving member; a camera module for capturing an image of the illuminated diagnostic assay placed in the receiving member; a processor for receiving the captured image from the camera module and determining whether or not a target analyte was present in the diagnostic assay captured by the camera module; and memory storing firmware, the firmware including a brightness compensation module configured to adjust the intensity of an image of a diagnostic cartridge captured by the camera module, in order to emulate a uniform field of illumination
(Continued)

over the diagnostic cartridge. The brightness compensation module is configured to adjust the intensity of the captured image based on an illumination compensation look-up table.

20 Claims, 8 Drawing Sheets

(51) Int. Cl.
    *G01N 21/27*     (2006.01)
    *G01N 21/84*     (2006.01)

(56) References Cited

U.S. PATENT DOCUMENTS

| | | | |
|---|---|---|---|
| 2005/0010995 A1 | 5/2005 | Fish et al. | |
| 2005/0110998 A1* | 5/2005 | Lin | G01N 21/6428 356/417 |
| 2008/0013092 A1 | 1/2008 | Maltezos et al. | |
| 2014/0128596 A1 | 5/2014 | Zuk | |
| 2015/0212074 A1* | 7/2015 | Xiang | G01N 21/6456 436/501 |
| 2018/0008687 A1* | 1/2018 | Ghoroghchian | A61K 47/60 |

FOREIGN PATENT DOCUMENTS

| | | |
|---|---|---|
| WO | WO 2004/017374 | 2/2004 |
| WO | WO 2011/128893 | 10/2011 |
| WO | WO 2014/015420 | 1/2014 |
| WO | 2014/037820 | 3/2014 |

OTHER PUBLICATIONS

Model M A et al., (2001) "A standard for calibration and shading correction of a fluorescence microscope", Cytom, Alan Liss, New York, Us, 44(4):309-316.

Wilkinson et al., (1994) "Shading correction and calibration in bacterial fluorescence measurement by image processing system", Computer Methods and Programs in Biomedicine, Elsevier, Amsterdam, NL, 44(2):61-67.

\* cited by examiner

DEVICE FOR READING AN IVD ASSAY

TECHNICAL FIELD

Described embodiments generally relate to optical read systems for reading diagnostic assays. In particular, described embodiments relate to systems for measuring the results of In-Vitro Diagnostics (IVD) assays.

BACKGROUND

For certain diagnostic assays, for example influenza and many sexually transmitted diseases, a clinician would ideally require immediate or very rapid test results to be obtained. This may be for public health reasons to minimise the spread of infection, and to ensure rapid therapeutic treatment for the patient. In remote locations, there may not be a clinical pathology infrastructure near the point of testing, and delays in obtaining test results for some infections could be harmful or even life-threatening to the patient, as well as harmful to the general public.

Rapid tests are available for many medical conditions, and may be procured at low cost. These tests are typically referred to as lateral flow tests, also known as lateral flow assays, membrane based assays, and lateral immunochromatographic tests.

Such tests are traditionally composed of a variety of materials overlapping onto one another and mounted on a backing strip. When a test is run, a sample containing a suspected antigen is added to a sample application pad. The sample migrates to a conjugate pad, where a particulate labelled conjugate specific to the target has been immobilized. The sample remobilizes the conjugate, and the analyte in the sample interacts with the conjugate as both migrate along a porous membrane. A capture reagent, having been laid down in a strip on the membrane at a test line location, serves to capture the analyte and conjugate as they migrate past. Accordingly, if the suspected antigen is present, a visible test line appears.

Whilst such tests offer rapid results, a problem with lateral flow tests is that a significant amount of the antigen or antibody must be present in the sample analyte in order for the development of a visible line. Consequently, these types of tests have a poor degree of sensitivity, resulting in a substantial number of false negative results, especially when a patient is in the early stages of an infection, and when the amount of a particular antigen, antibody or viral load in a patient may be low. Moreover, it is in the early stages of detection that it is important that diagnosis is correctly performed in order to administer an appropriate therapeutic to the patient, or to quarantine the patient to prevent the further spread of the infectious disease to the remainder of the community.

To address this problem, some manufacturers have developed lateral flow tests that employ fluorescent labels to facilitate the detection of an analyte along with appropriate readers. Although these labelling techniques can yield several orders of magnitude increase in sensitivity improvement relative to previous techniques, the complex and often expensive readers required for fluorescent detection have limited the market for such tests. The high cost of such readers detracts from the main benefit of lateral flow testing, which is that it is based on a low cost, robust and easy to use system.

One type of fluorescent reader previously developed for scanning the fluorescent response of an immunoassay performed in a micro titre plate (MTP) is disclosed in U.S. Pat. No. 4,626,684 (the Landa patent). This patent teaches a scanning optical fluorescent reader comprising illumination for exciting a plurality of immunoassay samples in combination with a fluorescence emission analysing means. In the Landa patent, the MTP can be driven by a motion system in one direction with the fluorescent scanner head driven by a motion system in an orthogonal direction, thereby providing bi-axial scanning motion capability. The problem with such scanning type readers is that the scanning mechanism adds unwanted cost and complexity to the reader, with the risk of component failure or in-field maintenance issues due to moving parts. Furthermore, if the scanning system is bumped or dislodged, positional errors can arise thereby affecting the accuracy of the assay.

An imaging optical reader is another kind of optical reading device, which is capable of detecting a two-dimensional array on a substrate. The imaging optical reader comprises an exciting light source, e.g. a xenon lamp, for illuminating a large part of the surface area (or the entire surface area) of the substrate, and a detector capable of detecting emitted light from the entire detection site-area simultaneously. An example of such an optical reader is a CCD (Charged-Coupled Device)-imager, which offers high quantum efficiency, sensitivity and spatial resolution. Further, a wideband light source may be provided with wavelength filters to provide monochromatic radiation. Such fluorescent imaging optical devices have been used in some fluorescent microscopy systems using confocal imaging approaches. These fluorescent optical imaging devices typically employ a range of high-cost thin-film interference filters (TFIFs) for filtering of the excitation light, and for filtering the emitted fluorescent light from the sample. Typically, filter sets used include an excitation filter for the light source, a dichroic mirror or beam splitter (where confocal imaging arrangements are used), and an emission filter for the emitted fluorescent light.

It is desired to address or ameliorate one or more shortcomings or disadvantages associated with prior systems and devices for reading diagnostic assays, or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Some embodiments relate to a system for reading fluorescent-labelled diagnostic assays for in-vitro diagnostic applications, the system comprising:
  a receiving member adapted to receive a fluorescent-labelled diagnostic assay cartridge carrying a fluorescent-labelled diagnostic assay;
  at least one excitation module configured to illuminate the diagnostic assay, when the diagnostic assay cartridge is placed in the receiving member;
  a camera module for capturing an image of the illuminated diagnostic assay placed in the receiving member;

a processor for receiving the captured image from the camera module and determining whether or not a target analyte was present in the diagnostic assay captured by the camera module; and memory storing firmware, the firmware including a brightness compensation module configured to adjust the intensity of an image of a diagnostic cartridge captured by the camera module, in order to emulate a uniform field of illumination over the diagnostic cartridge;

wherein the brightness compensation module is configured to adjust the intensity of the captured image based on an illumination compensation look-up table.

Some embodiments relate to an apparatus for reading fluorescent-labelled lateral flow diagnostic assays for in-vitro diagnostic applications, the system comprising:

a receiving member adapted to receive a fluorescent-labelled lateral flow diagnostic assay cartridge carrying a fluorescent-labelled diagnostic assay;

at least two excitation modules counter-disposed at an oblique angle to the receiving member and configured to illuminate the diagnostic cartridge, when the diagnostic assay is placed in the receiving member; and a camera module for capturing an image of the illuminated diagnostic assay placed in the receiving member.

Some embodiments relate to a system for reading fluorescent-labelled diagnostic assays for in-vitro diagnostic applications, the system comprising:

a receiving member adapted to receive a fluorescent-labelled diagnostic assay cartridge carrying a fluorescent-labelled diagnostic assay;

at least one excitation module configured to illuminate the diagnostic assay, when the diagnostic assay cartridge is placed in the receiving member;

a camera module for capturing an image of the illuminated diagnostic assay placed in the receiving member; and a processor for receiving the captured image from the camera module and determining whether or not a target analyte was present in the diagnostic assay captured by the camera module.

The camera module may comprise a CMOS camera module.

Each excitation module may comprise a light source having a maximum power rating of between around 0.1 Watts and around 5 Watts, such as around 0.1, 0.2, 0.3, 0.4, 0.5, 0.6, 0.7, 0.8, 0.9, 2, 3, 4 or 5 Watts, for example. In some embodiments, each excitation module may comprise a light source having a maximum power rating of at least 0.1 Watts. In some embodiments, each excitation module may comprise a light source having a maximum power rating of at least 0.9 Watts. In some embodiments, each excitation module may comprise a light source having a maximum power rating of at least 1 Watt. In some embodiments, each excitation module may comprise a light source having a maximum power rating of around 3 Watts.

The parts of the system may be configured to be substantially fixed relative to one another while the camera module captures an image of the diagnostic assay.

The system may comprise at least two excitation modules.

The excitation modules may each be counter-disposed at an oblique angle to the receiving member.

The angle of each excitation module to a horizontal plane of the receiving member may be between 30° and 60°. The angle of each excitation module to a horizontal plane of the receiving member may be around 45°.

The camera module may be mounted directly over the receiving member.

The system may include memory storing firmware. The firmware may include a brightness compensation module configured to adjust the intensity of an image of the diagnostic assay captured by the camera module, in order to emulate a uniform field of illumination over the diagnostic assay. The brightness compensation module may be configured to adjust the intensity of the captured image based on an illumination compensation look-up table. The illumination compensation look-up table may be generated based on a calibration image captured by the camera module, and is stored in the firmware.

The firmware may include an exposure control module for adjusting the exposure of an image captured by the camera module.

The firmware may include a colour decoding module for separating an image captured by the camera module into colour channels. The colour decoding module may be configured to discard data from one or more pre-determined colour channels.

Each excitation module may comprise at least one LED.

Each excitation module may comprise at least one light shaping element to produce a near-collimated beam of excitation light.

The at least one light shaping element may comprise a parabolic reflector.

The at least one light shaping element may comprise at least one lens. The at least one lens may comprise a plano-concave lens.

Each excitation module may comprise at least one optical filter. The at least one optical filter may comprise a dyed glass absorbance filter.

Some embodiments relate to an apparatus for reading fluorescent-labelled diagnostic assays for in-vitro diagnostic applications, the apparatus comprising:

a receiving member adapted to receive a fluorescent-labelled diagnostic assay cartridge carrying a fluorescent-labelled diagnostic assay;

at least two excitation modules configured to illuminate the diagnostic assay, when the diagnostic assay cartridge is placed in the receiving member; and a camera module for capturing an image of the illuminated diagnostic assay placed in the receiving member.

The excitation modules may each be counter-disposed at an oblique angle to the receiving member.

The angle of each excitation module to a horizontal plane of the receiving member may be between 30° and 60°. The angle of each excitation module to a horizontal plane of the receiving member may be around 45°.

The camera module may comprise a CMOS camera module.

Each excitation module may comprise a light source having a maximum power rating of between around 0.1 Watts and around 5 Watts, such as around 0.1, 0.2, 0.3, 0.4, 0.5, 0.6, 0.7, 0.8, 0.9, 2, 3, 4 or 5 Watts, for example. In some embodiments, each excitation module may comprise a light source having a maximum power rating of at least 0.1 Watts. In some embodiments, each excitation module may comprise a light source having a maximum power rating of at least 0.9 Watts. In some embodiments, each excitation module may comprise a light source having a maximum power rating of at least 1 Watt. In some embodiments, each excitation module may comprise a light source having a maximum power rating of around 3 Watts.

The parts of the apparatus may be configured to be substantially fixed relative to one another while the camera module captures an image of the diagnostic assay.

The camera module may be mounted directly over the receiving member.

The apparatus may include a processor for receiving the captured image from the camera module and determining whether or not a target analyte was present in the diagnostic assay captured by the camera module.

The apparatus may include memory storing firmware. The firmware may include a brightness compensation module configured to adjust the intensity of an image of the diagnostic assay captured by the camera module, in order to emulate a uniform field of illumination over the diagnostic assay. The brightness compensation module may be configured to adjust the intensity of the captured image based on an illumination compensation look-up table. The illumination compensation look-up table may be generated based on a calibration image captured by the camera module, and is stored in the firmware.

The firmware may include an exposure control module for adjusting the exposure of an image captured by the camera module.

The firmware may include a colour decoding module for separating an image captured by the camera module into colour channels. The colour decoding module may be configured to discard data from one or more pre-determined colour channels.

Each excitation module may comprise at least one LED.

Each excitation module may comprise at least one light shaping element to produce a near-collimated beam of excitation light.

The at least one light shaping element may comprise a parabolic reflector.

The at least one light shaping element may comprise at least one lens. The at least one lens may comprise a plano-concave lens.

Each excitation module may comprise at least one optical filter. The at least one optical filter may comprise a dyed glass absorbance filter.

According to some embodiments, the processor may be located within an external processing device remote from each of the receiving member, the at least one excitation module and the camera module.

According to some embodiments, the processor may be configured to determine whether or not a target analyte was present in the diagnostic assay captured by the camera module by determining a light emission level in an area of the image corresponding to a test zone of the diagnostic assay. According to some embodiments, the processor may be configured to determine whether or not a target analyte was present in the diagnostic assay captured by the camera module by comparing the light emission level in an area of the image corresponding to a test zone of the diagnostic assay with a predetermined light emission level. According to some embodiments, the processor may be configured to retrieve the predetermined light emission level from a memory device.

According to some embodiments, the processor may be configured to determine whether or not the diagnostic assay captured by the camera module was correctly processed by determining a light emission level in an area of the image corresponding to a control zone of the diagnostic assay. According to some embodiments, the processor may be configured to determine whether or not the diagnostic assay captured by the camera module was correctly processed by comparing the light emission level in an area of the image corresponding to the control zone of the diagnostic assay with a predetermined control light emission level. According to some embodiments, the processor may be configured to retrieve the predetermined control light emission level from a memory device.

According to some embodiments, each of the at least one excitation modules may be configured to illuminate the diagnostic assay, when the diagnostic assay cartridge is positioned in the receiving member. In some embodiments, each of the at least one excitation module may be positioned and angled to illuminate the diagnostic assay, when the diagnostic assay cartridge is positioned in the receiving member.

According to some embodiments, each of the at least two excitation modules may be configured to operate contemporaneously to illuminate the diagnostic assay. According to some embodiments, each of the at least two excitation modules may be configured to illuminate the diagnostic assay contemporaneously.

According to some embodiments, each of the at least two excitation modules comprise a light source, wherein each light source may be substantially identical.

DETAILED DESCRIPTION

Described embodiments generally relate to optical read systems for reading diagnostic assays. In particular, described embodiments relate to systems for measuring the results of In-Vitro Diagnostics (IVD) assays.

Figure 1:
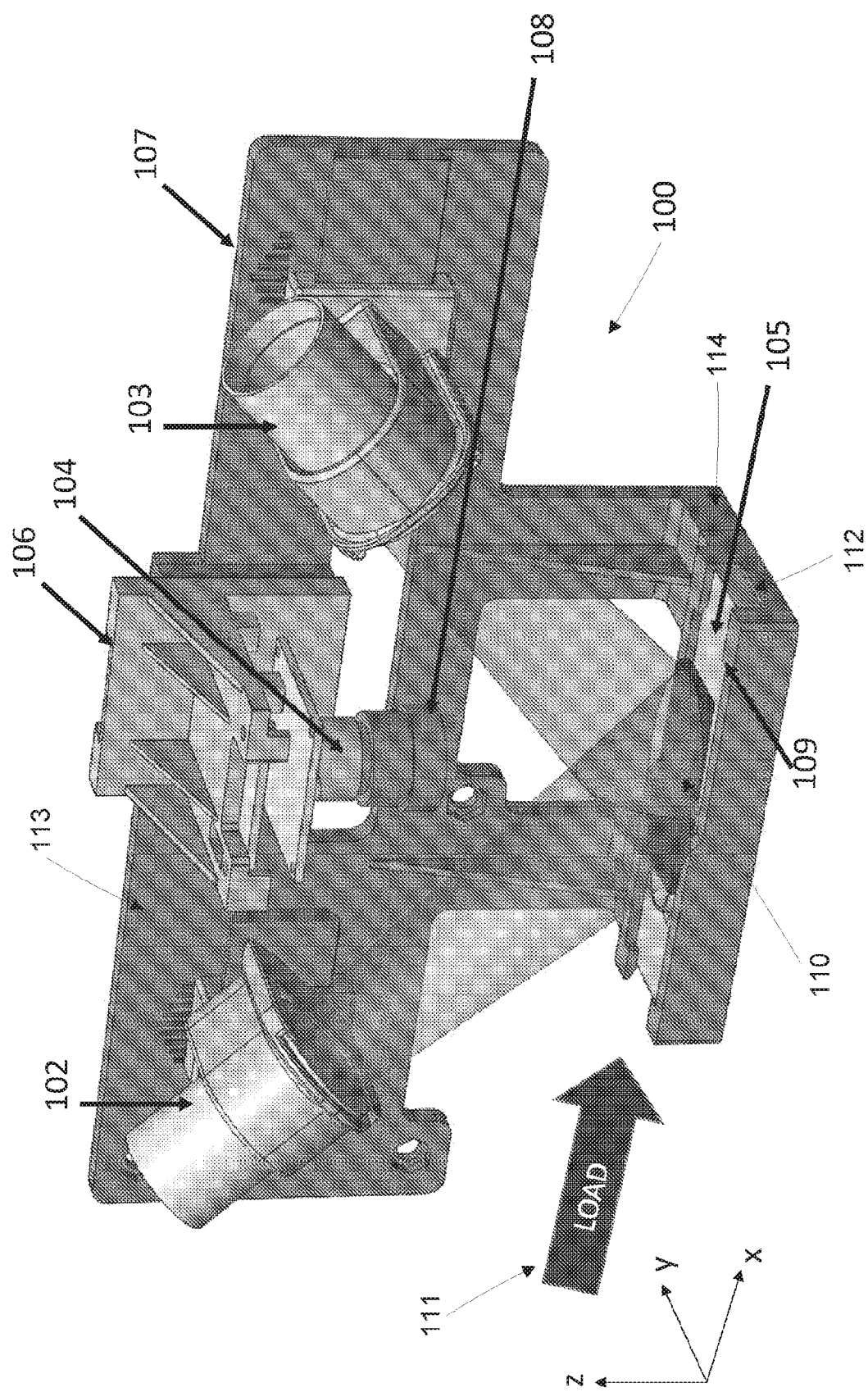
FIG. 1 is an isometric view showing the key elements of an optical read system according to some embodiments.

FIG. 1 shows an optical read system 100 for reading diagnostic assays according to some embodiments. The optical read system 100 may typically be housed within a benchtop instrument (not shown) which would include further various mechanical and electronic components to process the electronic results derived from the optical read system 100, and to display the results of an assay to an operator. The benchtop instrument may comprise a light-sealed housing for optical read system 100. These further components for the benchtop instrument, which may include plastic enclosures to make the assembly light-proof, mounting components, embedded computing modules, touchscreens, sliding drawers and the like, may be well known components, and are not further described in this document.

Optical read system 100 includes a number of modules, such as fluorescent excitation modules 102 and 103. Fluorescent excitation modules 102 and 103 are counter-disposed on either side of and at equal and opposite oblique angles to a receiving recess 112 that is configured to receive a diagnostic cartridge 105. Diagnostic cartridge 105 may contain a lateral-flow assay, which may be a fluorescent lateral-flow assay in some embodiments. In some embodiments, diagnostic cartridge 105 may be a fluorescent-labelled diagnostic assay cartridge, and may carry a fluorescent-labelled diagnostic assay. In some embodiments, diagnostic cartridge 105 may be a fluorescent-labelled lateral flow diagnostic assay cartridge, and may carry a fluorescent-labelled lateral flow diagnostic assay. In some other embodiments, another form of assay for in-vitro diagnostic (IVD) applications may be used. For example, molecular diagnostic assays with an amplified target present in a well of a microfluidic device, on-chip or on-slide hybridisation assays as microarrays, or assays in multi-well plates may be used by system 100 to determine and/or measure the fluorescent response of an analyte target.

According to some embodiments, receiving recess 112 may be adapted to receive a particular type of assay cartridge. For example, receiving recess 112 may be adapted to receive a fluorescent-labelled lateral flow diagnostic assay cartridge carrying a fluorescent-labelled diagnostic assay. Receiving recess 112 may be shaped and sized to receive a fluorescent-labelled lateral flow diagnostic assay cartridge and to hold the cartridge securely.

Lateral flow strip formats are used for qualitative and semi-quantitative assays and may use visual or fluorescent-labelled detection schemes. Lateral flow assays may involve the application of a liquid test sample suspected of containing the analyte to be detected to an application zone of a porous test strip. The strip may comprise a matrix material, which may be nitrocellulose, for example, through which the test fluid and analyte suspended or dissolved in the test fluid can flow by capillarity from the application zone to a capture zone where a detectable signal, or the absence of such, may reveal the presence of the analyte. According to some embodiments, the strip may include means for immunospecifically binding the analyte to be detected with a specific binding partner which bears the detectable label. The simple "one step" nature of lateral flow assays (which involves wicking of the sample unidirectionally along a porous strip) is considerably different to other immunoassay formats such as microarrays.

A microarray may be a 2D array on a solid substrate phase, which may be a glass slide, or the bottom of the well of a micro-titre plate, for example. Microarrays process large amounts of biological material, and their use commonly involves multiple steps such as washing, drying, and incubation. Microarrays are accordingly more complex to use than lateral flow assays, and can multiplex larger numbers of potential analyte targets than is currently possible for lateral flow assays. Microarrays may be used as a high-throughput screening tool, and may be used to assess genetic predisposition, to measure the expression levels of large numbers of genes simultaneously or to genotype multiple regions of a genome through the use of DNA and/or RNA. Microarrays may use relative quantitation in which the intensity of a feature is compared to the intensity of the same feature under a different condition, and the identity of the feature is known by its position. For example, two-colour microarrays or two-channel microarrays may be hybridized with cDNA prepared from two samples to be compared (e.g. diseased tissue versus healthy tissue) and that are labelled with two different fluorophores. Fluorescent dyes used for cDNA labelling include Cy3, which has a fluorescence emission wavelength of 570 nm (corresponding to the orange part of the light spectrum), and Cy5 with a fluorescence emission wavelength of 670 nm (corresponding to the red part of the light spectrum). Two Cy-labelled cDNA samples may be mixed and hybridized to a single microarray which may then be scanned in a microarray scanner to visualize fluorescence of the two fluorophores after excitation with a laser beam of a defined wavelength. Relative intensities of each fluorophore may then be used in ratio-based analysis to identify up-regulated and down-regulated genes.

In some embodiments, a longitudinal angle of each excitation module 102 and 103 is at between 30° and 60° to a horizontal plane of receiving recess 112. Preferably, a longitudinal angle of each excitation module 102 and 103 is at around 45° to a horizontal plane of receiving recess 112. Fluorescent emission from a viewing window 110 of diagnostic cartridge 105 excited by modules 102 and 103 is detected within an image captured by a CMOS camera module 104. In some embodiments, CMOS camera module 104 may be a CMOS array photodetector. In some embodiments, the images may be captured by a CCD camera module, or an alternative camera module.

CMOS camera module 104 may have a resolution of at least 5 Megapixels in some embodiments, having an image sensor array of at least 2560 pixels long×1920 pixels wide. In some embodiments, viewing window 110 of diagnostic cartridge 105 may be around 50 mm long, so that images captured by CMOS camera module 104 contain at least 2500 pixels per $mm^2$. In some embodiments, the image field may be 1000 pixels long×500 pixels wide. In some embodiments, the color depth or grey scale intensity range of CMOS camera module 104 may be between 8 and 12 bits per pixel, giving between 255 and 4096 grey levels on each pixel. In some embodiments, CMOS camera module 104 may be similar to the low cost cameras used in cellular telephones. CMOS camera module 104 may include a black and white camera in some embodiments. In some alternative embodiments, CMOS camera module 104 may include a colour camera.

Low cost CMOS cameras are typically two orders of magnitude lower in cost than high-end CCD cameras, including peltier-cooled CCD cameras conventionally used in fluorescent optical imaging. Furthermore, with such low cost CMOS cameras, no complex ancillary systems such as camera thermoelectric coolers are required. This enhances the reliability of optical read system 100, and makes it more suited to environments such as in-field testing, or clinics in developed countries without air conditioning, where ambient temperature changes would otherwise affect camera performance.

In some diagnostic applications, optical read system 100 may be configured to measure the actual colour of each image captured by CMOS camera module 104 in the zone where an analyte response is expected. This may particularly be for embodiments where multiplexed colour responses are required. In order to do this using a low cost 8 bit CMOS colour camera, colour response may be represented as an intensity level from 0 to 255 on each of the RGB channels. In this way, optical read system 100 can delineate over 16.5 million unique colours, and firmware 740 (described in further detail below with reference to FIG. 7) enables a colour change response of an analyte target to be measured.

Furthermore, colour decoding module 748 of firmware 740 may be configured to subtract undesired colours from the captured images (for example, subtracting the pink colour of red blood cells in a sample, or subtracting the yellow colour value of urine).

Modules 102, 103 and 104 may be mounted on a chassis 107 to ensure that they are in correct geometric alignment with each other, and with respect to diagnostic cartridge 105. Chassis 107 may have first and second plane components perpendicularly disposed to one another, such as a first horizontal plane component 113 and a second vertical plane component 114. Horizontal plane component 113 may define receiving recess 112 to receive diagnostic cartridge 105, which may be a channel-like receiving recess in some embodiments. In some other embodiments, system 100 may alternatively include a bracket, clamp, or other form of receiving member for holding diagnostic cartridge 105.

Vertical plane component 114 may support excitation modules 102 and 103, and CMOS camera module 104. In some embodiments, excitation modules 102 and 103 may be mounted on either side of CMOS camera module 104. CMOS camera module 104 may be mounted on a slidable bracket 106 to allow a height of CMOS camera module 104 to be adjusted in relation to the position of receiving recess 112. Excitation modules 102 and 103 may be mounted at a similar height from receiving recess 112 as CMOS camera module 104. In some embodiments, CMOS camera module 104 and excitation modules 102 and 103 may be positioned at a distance of between around 50 mm and 150 mm from receiving recess 112.

In some embodiments, chassis 107 is configured so that the space between CMOS camera module 104 and receiving recess 112 is unobstructed, to allow CMOS camera module 104 to take unobstructed images of diagnostic cartridge 105 positioned in receiving recess 112. In some embodiments, chassis 107 may be configured so that the space between each excitation module 102 and 103 and receiving recess 112 is unobstructed, to allow light from each excitation module 102 and 103 to travel to diagnostic cartridge 105 positioned in receiving recess 112 unobstructed.

In some embodiments, excitation modules 102 and 103 may be mounted on slidable and/or pivotable brackets to allow the position and orientation of excitation modules 102 and 103 to be adjusted and fixed with respect to receiving recess 112. In some embodiments, the position and orientation of horizontal plane component 113 may be adjustable with respect to vertical plane component 107, to allow the height and/or orientation of receiving recess 112 to be adjusted with respect to the position of excitation modules 102 and 103, and CMOS camera module 104.

Excitation modules 102 and 103 provide fluorescent excitation energy to excite a fluorescent analyte target present in viewing window 110 of diagnostic cartridge 105. In some embodiments, diagnostic cartridge 105 may contain a microarray having multiple small dots, where each dot corresponds to a different analyte target, allowing the results of the analyte concentration for each dot to be determined independently.

Preferably, excitation modules 102 and 103 comprise high power light emitting diodes (LEDs) 204 (best shown in FIG. 2) having a maximum power rating of at least 1 Watt. According to some embodiments, excitation modules 102 and 103 comprise a light source wherein each light source may be identical or substantially identical. For example, according to some embodiments, each excitation module 102 and 103 may comprise a 365 nm high power LED. In some embodiments, LEDs 204 may have a maximum power rating of at least 2 Watts, 3 Watts, 4 Watts, 5 Watts. or more. In some embodiments, LEDs 204 may have a maximum power rating of at least 0.1 Watts, and in some embodiments, LEDs 204 may have a maximum power rating of at least 0.2 Watts, 0.3 Watts, 0.4 Watts, 0.5 Watts, 0.6 Watts, 0.7 Watts, 0.8 Watts, or 0.9 Watts. In some embodiments. LEDs 204 may have a maximum power rating of between around 0.1 Watts and around 5 Watts, such as around 0.1, 0.2, 0.3, 0.4, 0.5, 0.6, 0.7, 0.8, 0.9, 2, 3, 4 or 5 Watts, for example.

Figure 2:
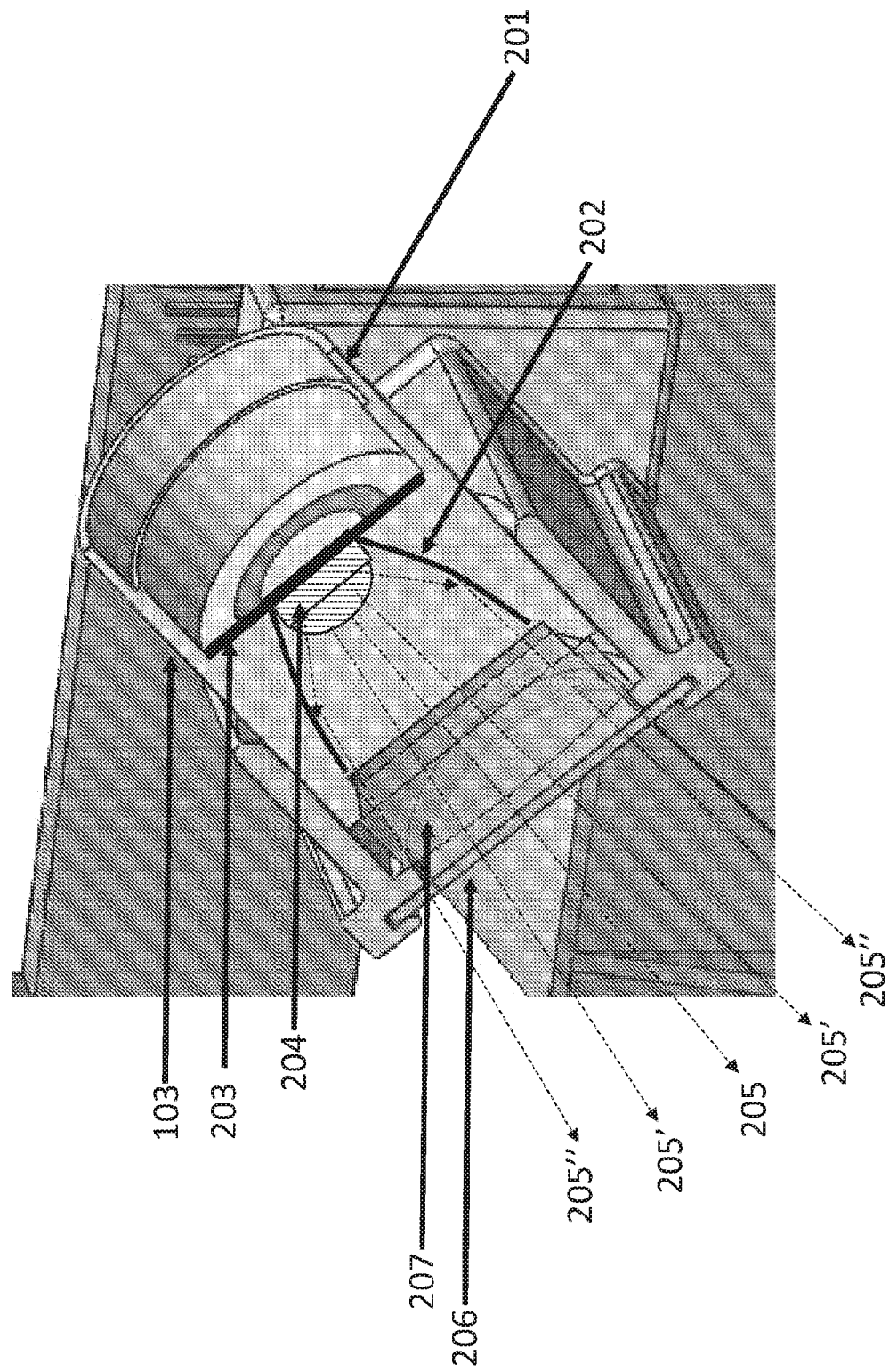
FIG. 2 is an isometric view of the excitation module of the optical read system of FIG. 1.

Each excitation module 102 and 103 may further comprise one or more beam shaping elements (for example, reflectors 202, lenses 207, and diffusers), as well as fluorescent excitation filters 206, which are further explained in relation to FIG. 2.

The use of LEDs having a power rating of at least 1 W allows excitation modules 102 and 103 to produce a high density of fluorescent excitation energy over a relatively large window area (for example, 40 mm long×20 mm wide in some embodiments). For fluorescent targets used in diagnostic assays, the fluorescently-emitted response from the analyte target is in direct proportion to the fluorescent excitation energy striking the analyte target. Accordingly, the use of high power LEDs 204 enables lower analyte concentrations to be detected as a fluorescent signal, whereas such fluorescent emission signal would not be present using a conventional low-power LED (such as a 5 mm or 3 mm round dome type LED). The latter conventional LED type can only produce low density fluorescent excitation energy when positioned remotely from diagnostic cartridge 105, even when the conventional LEDs also use beam shaping elements. Accordingly, the use of new-generation high power LEDs 204 having a power rating of at least 1 W allows a system which has significantly improved diagnostic sensitivity to detect lower analyte concentrations than would be the case if conventional low-power LEDs were used.

Excitation modules 102 and 103 may produce near-collimated light beams 301 and 302 (shown in FIG. 3) exiting each module 102 and 103 with a high power density which thereby enables each of the excitation modules 102 and 103 to be positioned at a remote distance from viewing window 110. Such remote positioning thereby ensures that excitation modules 102 and 103 do not obscure the field of view of CMOS camera module 104. The production of such near-collimated excitation light using LEDs 204 and beam shaping elements 202 and 207 does not achieve perfectly-collimated light produced by coherent sources such as lasers and laser diodes. However, there are a number of advantages to LEDs compared to lasers and laser diodes, such as the lower cost of high power LEDs compared to lasers and laser diodes. Some firthet advantages include, for example, (i) much simpler and lower cost power supplies required to drive the light source; (ii) easier thermal management not requiring the use of cooling fans or thermoelectric coolers; (iii) simpler mounting systems; (iv) simpler assembly procedures which require less precise optical alignment arrangements; and (v) easier maintenance. The use of high power LEDs 204 and associated beam shaping elements may therefore be a better solution to reduce the overall cost and complexity of optical read system 100. However, in some embodiments, lasers, laser diodes, and other light sources may be used instead of or in addition to LEDs 204.

In some embodiments, optical read system 100 has at least two low excitation modules 102 and 103 counter-disposed, each at an opposed oblique angle to the viewing window 110, with camera module 104 mounted directly over viewing window 110. Because excitation sources 102 and 103 are each mounted at an oblique angle to viewing window 110, excitation light from each excitation module 102 and 103 generally reflects off viewing window 110 at a reflected (oblique) angle equal to the incident (oblique) angle. In this way, the reflected light from excitation modules 102 and 103 is not undesirably passed into camera module 104 above viewing window 110.

In some alternative embodiments, optical read system 100 may have only one low excitation module 102.

CMOS camera module 104 may also include a modular lens element 108. Modular lens element 108 may have an effective focal length to suit the particular diagnostic cartridge 105 being imaged. Furthermore, CMOS camera module 104 may be mounted on slidable bracket 106 to enable the camera module 104 to be set up in the factory at different heights to suit different diagnostic cartridges 105. For example, a macro lens having a short focal length may be used in combination with camera module 104 positioned closer to diagnostic cartridge 105 (without obscuring fluorescent excitation from modules 102 and 103) to take high resolution images of a small area.

Alternatively, a lens having a longer focal length with camera module 104 positioned further from diagnostic cartridge 105 may be used to capture larger areas—for example a larger area microarray. Furthermore, lens element 108 may preferably have a fluorescent emission filter as a separate filter element held within a housing of lens element 108, or further preferably the lens itself within lens element 108 may be a dyed-glass lens which also doubles as an absorbance emissions filter. Such simplifications reduce parts count, and reduce assembly complexity.

In some embodiments, a motion scanning stage is not required for optical read system 100. Diagnostic cartridge 105 may be manually pushed into a slot in the direction of the "LOAD" arrow 111, and an end stop 109 may be situated at one end of receiving recess 112 to reliably and repeatably position diagnostic cartridge 105 for imaging. Fiducial markers (not shown) may be printed on cartridge 105 to provide a reference point for camera module 104 to locate various test zones within viewing window 110 for subsequent image analysis in firmware. In some embodiments, optical read system 100 contains no moving parts, and therefore does not suffer from the undesirable cost, complexity, and field serviceability problems of previously used scanning type fluorescent readers which utilise motion-driven scanning stages that are usually driven by electric motors. The parts of system 100 may be configured to be substantially fixed relative to one another while CMOS camera module 104 captures an image of diagnostic cartridges 105.

Cartridge 105 or portions of chassis 107 in the field of view of camera 104 may include fluorescent calibration markers or inserts containing such markers (not shown) to evaluate the expected fluorescent response from the excitation modules 102 and 103.

Declining fluorescent response measured from such calibration markers may occur over the life of the instrument, for example due to declining LED output. This may be compensated for by scaling up the overall image intensity by a calibration adjustment factor which is the reciprocal of the factor due to any such decline in LED output. In such a way uniform fluorescent response of the system described in this invention can be expected over the life of the instrument. The image intensity calibration may be performed by a brightness compensation module 742 in firmware 740 of system 100, described in further detail below with reference to FIG. 7.

FIG. 2 shows a detailed cross-section view of excitation module 103 of optical read system 100. Excitation module 103 contains high-power LED 204. LED 204 is preferably a surface mount type LED mounted preferably on an aluminium substrate printed circuit board (PCB) 203 which has better heat transfer characteristics than a conventional PCB. In some embodiments, particularly for use with long Stokes shift fluorophores such as Europium and other lanthanide chelates, LED 204 may be a UV LED with a dominant excitation wavelength of around 365 nm. PCB 203 may be mounted within a housing 201 which may be manufactured from a metallic material such as aluminium to act as a heat sink for high power LED 204 for applications where LED 204 is powered continuously. Alternatively, in some embodiments LED 204 will only be powered briefly for "flash" illumination to allow CMOS camera module 104 to record an image. In such circumstances, LED 204 is only powered for a brief period, and housing 201 is not required to act as a heat sink, and accordingly may be molded from a lower cost plastic material.

LED 204 typically emits light at a broad range of angles. However, it may be required that LED 204 emits light in a near-collimated manner as shown in FIG. 1. Accordingly, an optional parabolic reflector 202 may be used to focus the light emitted by LED 204 into a near collimated beam. For example, light rays 205 and 205' exit LED 204 at a narrow angle, close to parallel to the longitudinal axis of excitation module 103. However light rays 205" exit LED 204 at a broader angle. These peripheral rays 205" emitted at an oblique angle collide with parabolic reflector 202 and are reflected away from excitation module 103 at a narrow angle also being close to parallel to the longitudinal axis of excitation module 103. Parabolic reflector 202 may be a molded plastic reflector with a metallised surface in some embodiments, and may be integrated with housing 201 as a unitary plastic moulding to reduce complexity and cost. Alternatively, parabolic reflector 202 may be a polished insert into an aluminium or other metallic housing 201. In some embodiments, a lens (not shown) may be used instead of or in addition to parabolic reflector 202.

As shown in FIG. 2, excitation module 103 has an optional lens 207. Optional lens 207 may be a plano-concave lens to spread the angle of the light emitted from LED 204 over a broader area on viewing window 110. This results in commensurately lower fluorescent excitation energy in viewing window 110. Alternatively, optional lens 207 may be a plano-convex lens to narrow the angle of the light emitted from LED 204 over a narrower area on viewing window 110. This results in commensurately higher fluorescent excitation energy in viewing window 110.

Excitation module 103 also has an excitation filter 206 to block any fluorescent excitation light from reaching camera 104, since such light would otherwise mask the presence of the fluorescent response from the analyte target, diagnostic cartridge 105. According to some embodiments, particularly for use with long Stokes shift fluorophores such as Europium and other lanthanide chelates, excitation filter 206 may be a dyed glass absorbance filter, as sharp wavelength cut-offs, or cut-ons, or pass-bands are not required for these fluorophores. In some other embodiments, excitation filter 206 may be a TFIF or another suitable filter. Excitation filter 206 may be dyed from a clear glass substrate, or from grit-blasted glass substrate. In the latter case, filter 206 may have some partial light diffusion characteristics to smooth the spread of light more uniformly over the image field.

Figure 3:
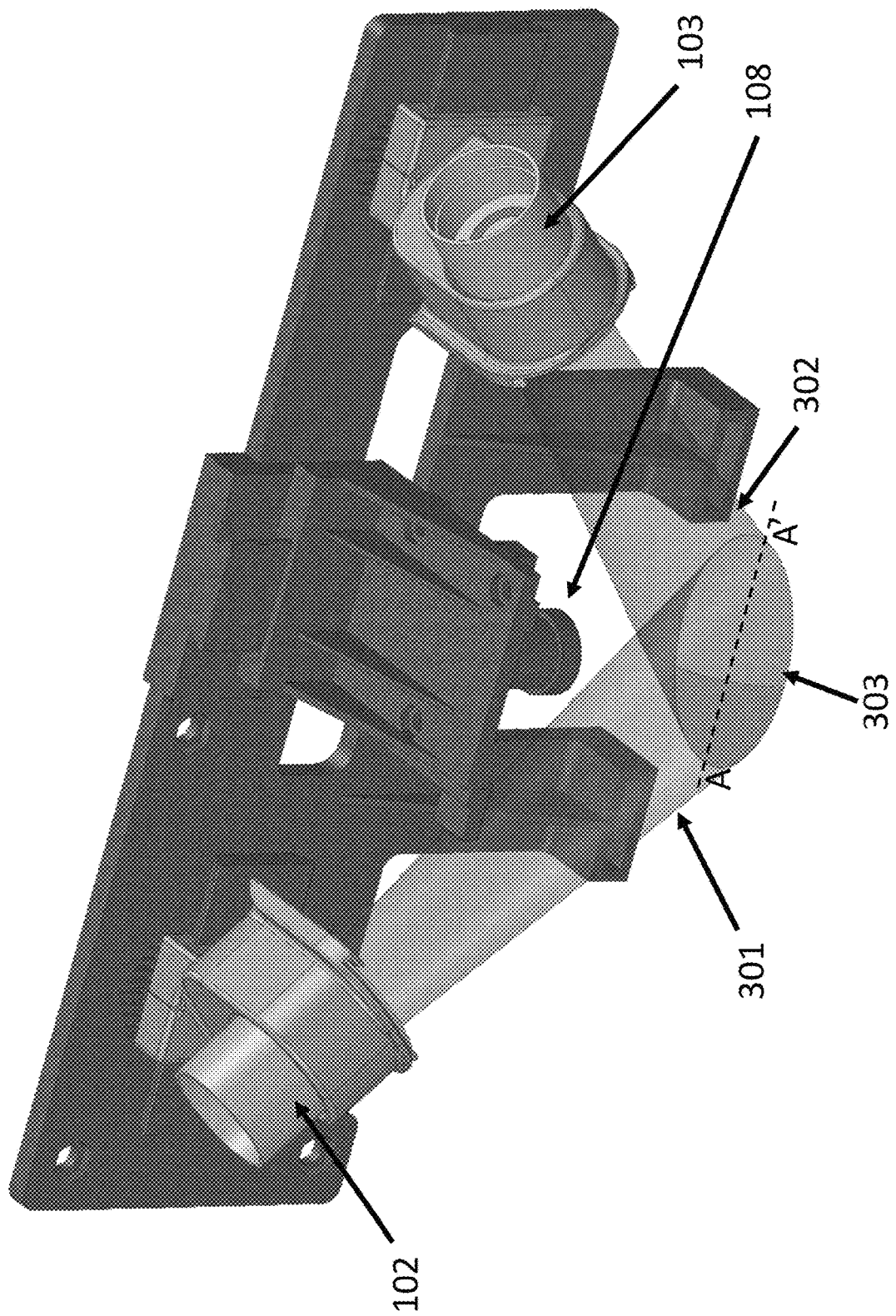
FIG. 3 is a further isometric view showing combinatorial fluorescent excitation from two counter-disposed excitation sources of FIG. 1.

FIG. 3 shows the combined light produced by excitation modules 102 and 103 operating in combination. Excitation modules 102 and 103 may be configured, through their positioning and angle, to illuminate a diagnostic assay, when diagnostic assay cartridge 105 is positioned in the receiving recess 112. Excitation modules 102 and 103 may be configured to operate contemporaneously, and to illuminate the diagnostic assay contemporaneously. Light produced by modules 102 and 103 is generally in the form of outwardly widening frustro-conical beams 301 and 302. These beams are truncated into an elliptical pool of light 303 in the horizontal plane at viewing window 110. Elliptical pool of light 303 has a major axis A-A' as shown in FIG. 3. Considering a case when excitation module 102 is operating solely (that is, with module 103 in the 'off' state), at position A on the major axis of pool of light 303 the light intensity produced by module 102 is relatively bright, whereas at position A' on the major axis the light intensity from module 102 is relatively dark. This is because light intensity diminishes with the square of distance from the light source. A' is furthest from module 102, whereas A is closest to module 102.

If only a single excitation module 102 or 103 was directing excitation light at viewing window 110, the result would be the production of a generally elliptical pool of light which would be generally relatively higher in intensity at the point on the outermost major axis of the ellipse proximal to excitation module 102 or 103, and generally lower in intensity at the point on the outermost major axis of the ellipse distal from excitation module 102 or 103. Consequently, if only one excitation module 102 or 103 was used, there would be a non-uniform field of illumination over viewing window 110. In such embodiments, a brightness compensation module 742 (as described below with reference to FIG. 7) may be used to compensate for the non-uniform field of illumination.

However, with both excitation modules 102 and 103 operating contemporaneously, relatively darker light at A' from module 102 is compensated for by relatively brighter light at A' from module 103. The same compensation occurs over the entire elliptical pool of light 303 in that the relatively darker/brighter light from one module 102/103 is always equally compensated for by relatively brighter/darker light from the counter-disposed module 102/103. In this way, a near uniform field of excitation light is achieved over the entire elliptical pool of light 303 as the result of the use of the counter-disposed excitation modules 102 and 102.

Figure 4:
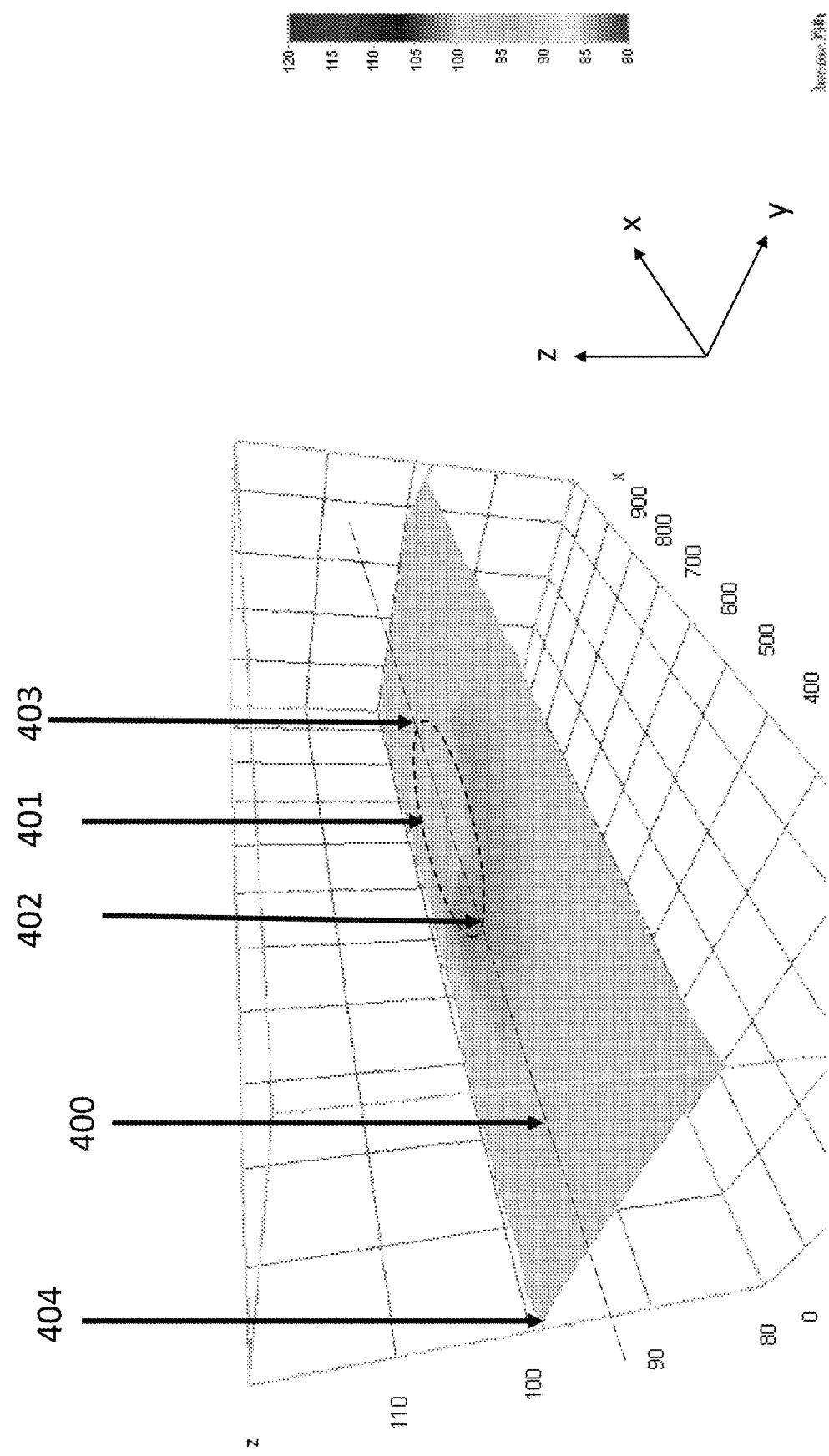
FIG. 4 is a three-dimensional plot showing the variation in light intensity over the read window of a diagnostic cartridge, where the fluorescent excitation was provided by the two counter-disposed excitation sources of FIG. 3.

FIG. 4 is a three-dimensional surface plot showing a light intensity map produced in an exemplary experiment. In this experiment, counter-disposed excitation modules 102 and 103 were set up in a proof of concept system (POC) similar to the system shown in FIG. 1. In this experiment, two counter-disposed modules 102 and 103 were used, each having a 3 W 365 nm high power LED 204. Each excitation module 102 and 103 comprised a parabolic reflector 202, a plano-concave lens 207, and a dyed glass excitation filter 206. Excitation modules 102 and 103 were housed in a matte black aluminium light-proof enclosure, and were directed at a 36 mm×15 mm viewing window 110, being a section of blank white card housed in a plastic diagnostic cartridge 105. Images were captured using a 5 Megapixel CMOS camera module 104 with 12 bits per pixel intensity levels (from 0-4096 counts). Images were analysed using the public domain image analysis package "Image J".

As illustrated in FIG. 4, despite the use of excitation modules 102 and 103 with substantially identical light sources, the intensity field over the surface of viewing window 110 is not perfectly uniform. For example, at the corners 404 of the image area, the brightness of the illumination dips down slightly. Conversely, in the centre of the field, there is a slightly centrally raised brighter portion 402 at the major axis of ellipse 401 which is brighter on one portion of the major axis of the ellipse 401 than at the opposite side of the major axis of the ellipse 403. The reason for this discrepancy is that the counter-disposed LEDs 204 are not perfectly matched, and therefore a perfectly uniform illumination field is not possible.

It is possible to compensate for the non-perfect illumination field shown in FIG. 4 by the use of a brightness compensation module 742 in firmware 740 of optical read system 100, described below in further detail with reference to FIG. 7.

Figure 5:
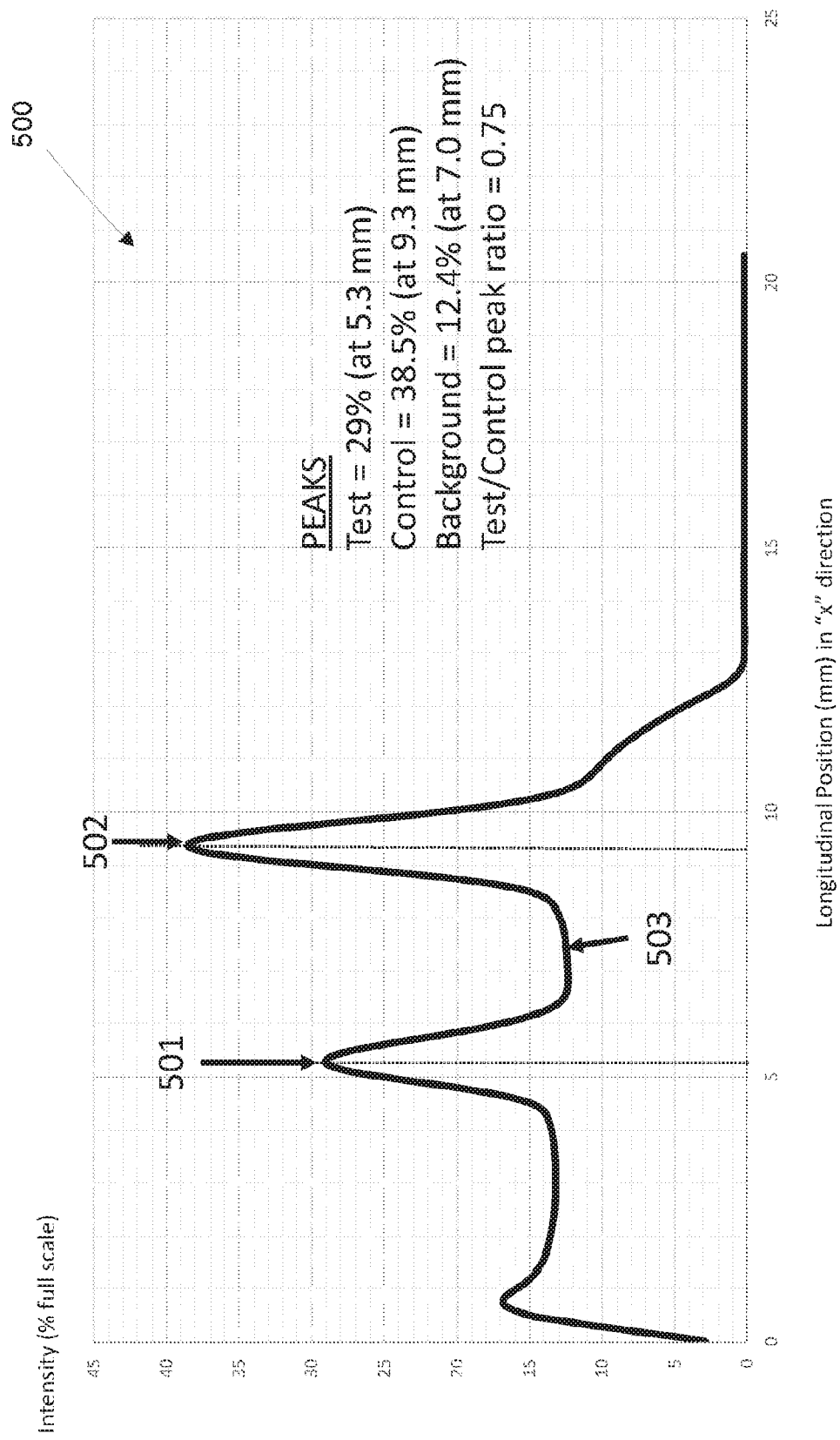
FIG. 5 is a plot of the variation of fluorescent emission against longitudinal position for a fluorescent assay read using a known optical reader, being the compact Point-Of-Care (cPOC) reader produced by LRE Esterline GMBH.
Figure 6:
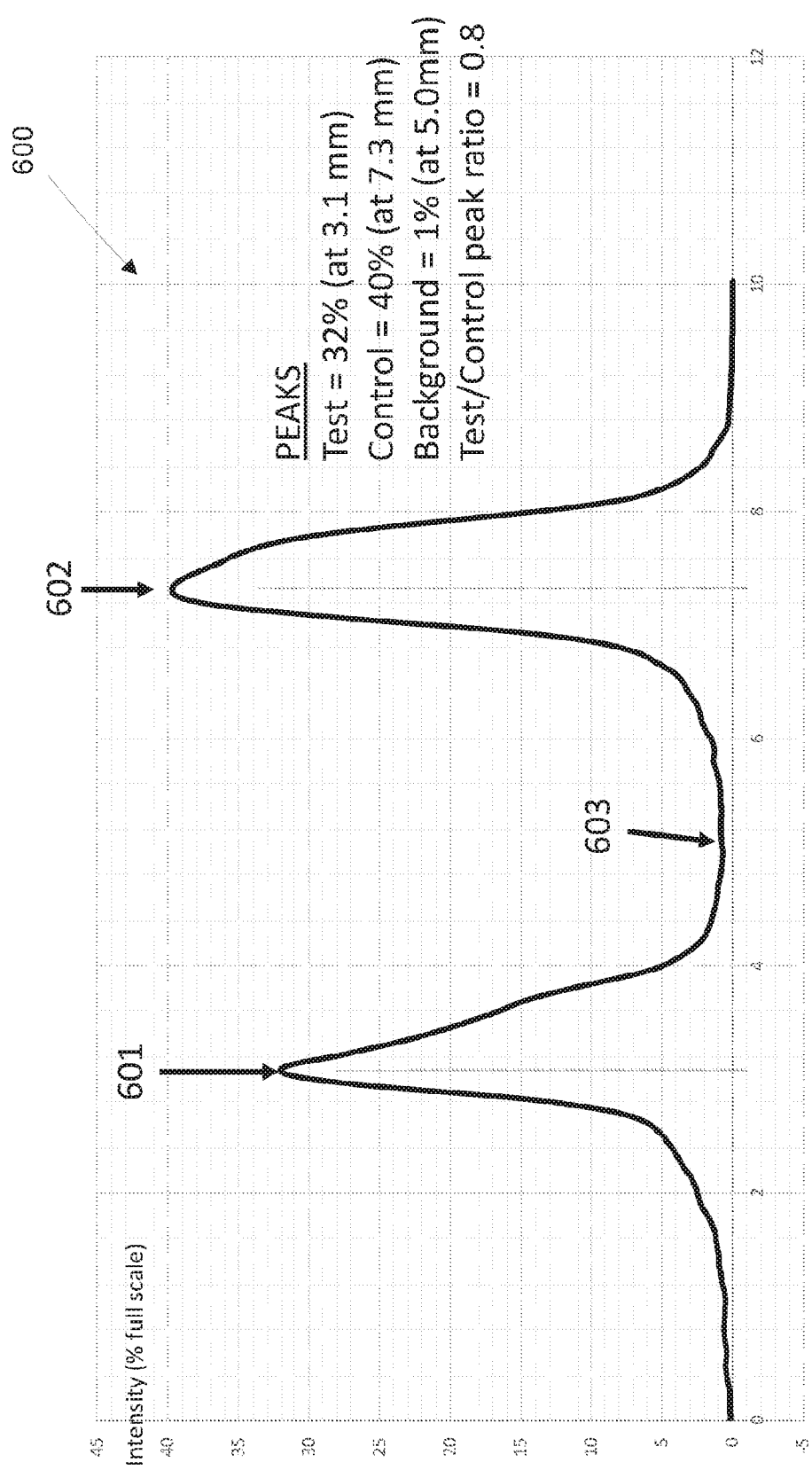
FIG. 6 is a plot of the variation of fluorescent emission against longitudinal position for the fluorescent assay of FIG. 5 read using the optical read system of FIG. 1.

FIGS. 5 and 6 show the results of a benchmarking exercise in which the performance of the fluorescent reader of the present application was compared to the performance of the cPOC fluorescent reader which was procured from LRE Esterline GmbH (Munich, Germany). Readers such as the cPOC reader and derivatives of such readers have previously been used commercially by lateral flow assay manufacturers.

In the tests illustrated in FIGS. 5 and 6, a Sofia hCG (human chorionic gonadotropin) assay produced by Quidel Corporation (LaJolla, USA) was used. Such assays are used in pregnancy testing. These assays are fluorescent lateral flow assays using an analyte target labelled with a Europium bead. Such beads are excited in UV wavelengths at 365 nm, and emit bright orange fluorescent light with a long Stokes shift to 615 nm. Urine samples were obtained from a pregnant female donor 33 weeks pregnant, and Quidel's Sofia test was run in accordance with the package insert.

FIG. 5 shows the result of running the Quidel Sofia hCG assay in the cPOC reader. A scan plot 500 shows that there is a test line peak 501 which registers a fluorescent response of 299 of the full scale reading (which is 1,048,576 counts). The assay also included a procedural control line as a quality assurance step, and this results in peak 502 which registers a fluorescent response of 38.5% of the full scale reading. Between the peaks 501 and 502 there is some background fluorescent response 503 due to non-specific binding, which registers a fluorescent response of 12.4%.

FIG. 6 shows the results of imaging an identical Quidel Sofia hCG assay for the same 33 weeks pregnant donor as imaged in FIG. 5. Images of the fluorescent response were taken using the POC system described above in relation to FIG. 4. Scan plot 600 of the results shows that there is a test line peak 601 which registers a fluorescent response of 32% of the full scale reading (which is 4.096 counts). The procedural control line results in peak 602 which registers a fluorescent response of 40% of the full scale reading. Between the peaks 601 and 602 there is some background fluorescent response 603 due to non-specific binding, which registers a fluorescent response of 1%.

In comparing FIGS. 5 and 6, it can be seen that optical read system 100 of the present application is a simplified optical reader compared to the cPOC reader, which uses a scanning type approach, that nonetheless produces accurate results for tests such as fluorescent lateral flow tests. Optical read system 100 can be manufactured with less complexity and cost compared to previously known readers, and this may be achieved without any compromises in diagnostic performance.

Figure 7:
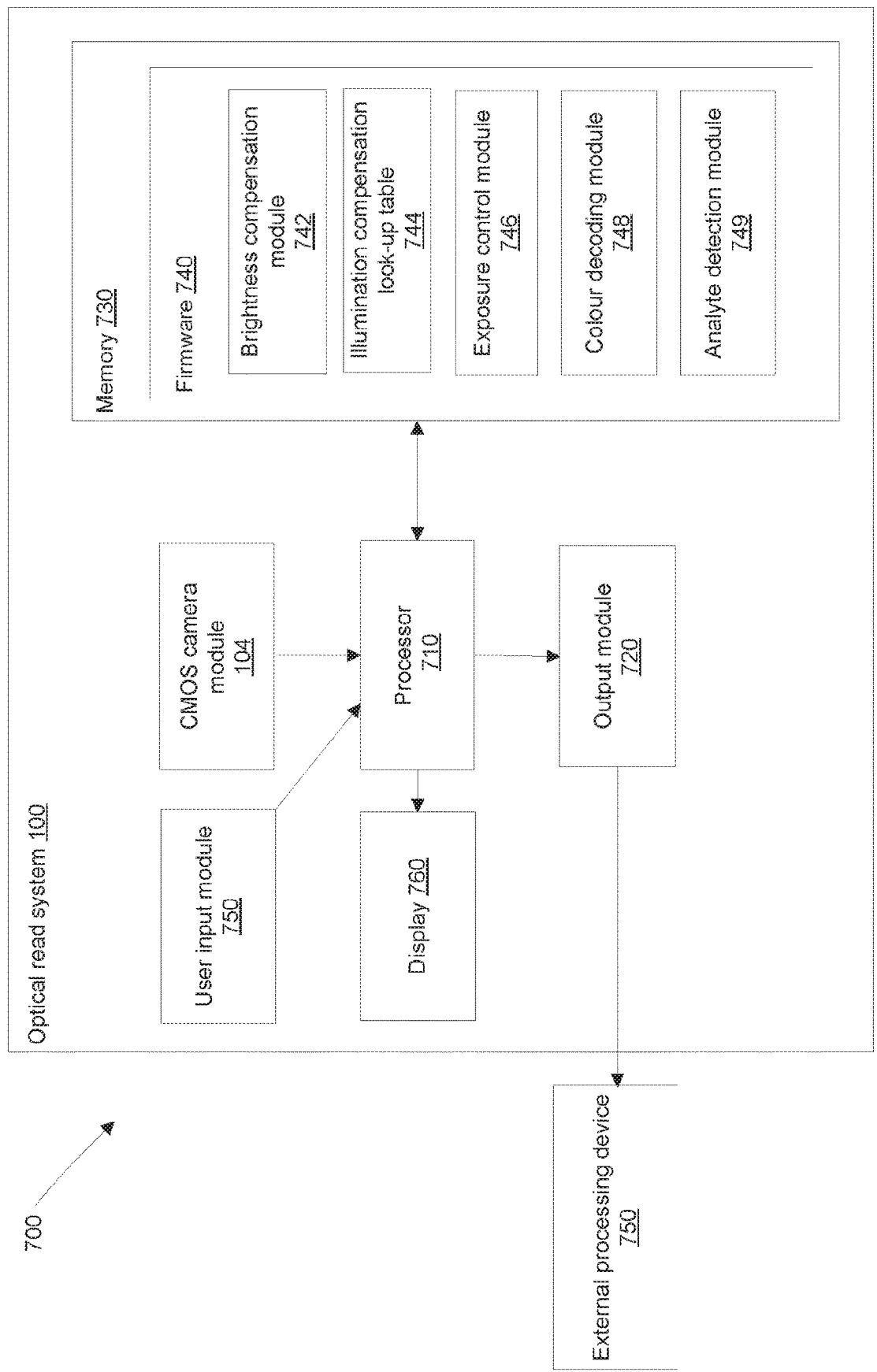
FIG. 7 is a block diagram of the computing components of the optical read system of FIG. 1.

FIG. 7 shows a block diagram of the computing components of optical read system 100, as well as an external processing device 750, which may be in communication with optical read system 100. Although only one external processing device 750 is shown, optical read system 100 may be in communication with more than one external processing device 750, which may in some embodiments be desktop or laptop computers, mobile or handheld computing devices, servers, distributed server networks, or other processing devices. In some cases, one or more external processing devices 750 may form part of the benchtop instrument (not shown) which houses external processing device 750.

Optical read system 100 may have a number of computing components, including a processor 710, and output module 720, memory 730, user input module 750 and display 760. In some alternative embodiments, optical read system 100 may be a simplified system with no processor 710, and outputs captured by CMOS camera module 104 may instead be output to an external device such as external processing device 750 for processing. For example, processor 710 may be located within external processing device 750, remote from other components of optical read system 100 such as receiving recess 112, excitation modules 102 and 103, and camera module 104.

Processor 710 may include one or more data processors for executing instructions, and may include one or more of a microprocessor, microcontroller-based platform, a suitable integrated circuit, and one or more application-specific integrated circuits (ASIC's). Processor 710 may receive inputs from CMOS camera module 104, as well as user input module 750 and other input sources, and may communicate with output module 720, memory 730 and display 760. User input module 750 may accept input from a number of user input sources, such as a touchscreen, keyboard, buttons, switches, electronic mice, and other user input controls. Output module 720 may allow for wired or wireless communication between optical read system 100 and external processing device 750, and may utilise Wi-Fi, USB, Bluetooth, or other communications protocols. Memory 730 may include one or more memory storage locations, either internal or external to optical read system 100, and may be in the form of ROM, RAM, flash or other memory types. Display 760 may include one or more screens, which may be LCD or LED screen displays in some embodiments. In some embodiments, system 100 may further include lights, speakers, or other output devices configured to communicate information to a user.

Memory 730 may be accessible to processor 710, and contain program code that is executable by processor 710, in the form of executable modules in firmware 740 of system 100. These executable modules may include a brightness compensation module 742, exposure control module 746 and colour decoding module 748. Firmware 740 may further store data accessible to processor 710, which may include an illumination look-up table 744.

According to some embodiments, illumination of diagnostic cartridge 105 by excitation modules 102 and 103 excites the fluorescent labels in the diagnostic assay within cartridge 105. Camera 104 captures an image of the illuminated diagnostic assay and processer 710 determines the level of fluorescence emission from the excited diagnostic assay to determine the presence, or absence, of the target analyte on the diagnostic assay captured by camera 104.

For example, in a fluorescent-labelled lateral flow diagnostic assay, if a target analyte is present in a sample, the analyte will bind a fluorescent-labelled antibody to form a complex. This fluorescent-labelled-antibody-analyte complex then flows along the membrane of diagnostic cartridge 105 and, if present, this complex then binds to capture antibodies that have been positioned on the membrane at a test zone/line.

Processor 710 may be configured to determine the signal level or light emission level of the fluorescence emission in a test zone, line or area of the captured image that corresponds to a test zone, line or area of the illuminated diagnostic assay, and compare the light emission level to a predetermined threshold. If the signal level meets or exceeds the predetermined threshold, processor 710 determines the presence, and/or amount of analyte present, or the absence of the target analyte in the sample. The predetermined threshold may be stored in memory 730, and processor 710 may be configured to retrieve the threshold value from memory 730.

A lateral flow assay typically also contains a control line or area to confirm that the assay has developed correctly and the assay is valid. The control line usually comprises antitype antibodies that bind the fluorescent-labelled antibody and/or any fluorescent-labelled antibody-analyte complex that has not bound to the test line. Therefore, processor 710 may further be configured to determine if an assay is valid or invalid by measuring the level of fluorescence emission at the control line position in the captured image. Processor 710 may be configured to determine a light emission level in an area of the captured image corresponding to the control line or control zone of the diagnostic assay. Processor 710 may be configured to determine whether or not the assay was correctly processed by comparing the light emission level with a predetermined control light emission level. If the signal level meets or exceeds the predetermined control threshold, processor 710 determines that the assay was processed correctly. The predetermined control threshold may be stored in memory 730, and processor 710 may be configured to retrieve the threshold value from memory 730.

Brightness compensation module 742 may be used by system 100 to compensate for a non-perfect illumination field, as shown in FIG. 4. During factory setup of system 100, CMOS camera module 104 may capture a calibration image, which is communicated to processor 710. Processor 710 may then calculate an average brightness of all pixels across the calibration image. This may produce an average grey scale value of INTave, which may be stored in memory 730. The brightness of each pixel having a location [x,y] in the captured image may be stored in memory 730 as INTxy. For each pixel [x,y] in the captured calibration image, a brightness scaling factor $BRI_{xy}=[INT_{ave}/INT_{xy}]$ may be determined by processor 710 and stored in illumination compensation look-up table (LUT) 744.

When diagnostic cartridge 105 is read, processor 744 may execute instructions stored in brightness compensation module 742 in order to scale the fluorescent response at any particular pixel location [x,y] by a factor $BRI_{xy}$, as read by processor 710 from illumination compensation LUT 744. Accordingly, processor 710 scales up the fluorescent response from pixels in relatively darker areas to compensate for the non-uniformity of the illumination field, and conversely, pixels in relatively brighter areas are scaled down by processor 710 to compensate for the non-uniformity of the illumination field. In this way, optical read system 100 emulates a perfectly uniform field of illumination. Brightness compensation module 742 thereby enhances the accuracy of the assay, in particular to deal with production variations such as variations in LED intensity. It also means that lower-specification LEDs (which are cheaper) may be used without impacting the accuracy of the overall system.

In some embodiments, brightness compensation module 742 may further be used to re-calibrate the brightness of each image captured based on calibration markers, as described above with reference to FIG. 1. When CMOS camera module 104 captures an image, processor 710 may determine the brightness of areas of the image that are known to correspond to areas where calibration markers are placed. The brightness values of these areas may then be compared with expected brightness values stored in memory 730, and a calibration adjustment factor may be calculated based on the difference between the measured values and the stored expected values. Processor 710 may subsequently execute brightness compensation module 742 to scale the overall image brightness based on the calibration adjustment factor. Based on this, brightness compensation module 742 may be used to compensate for decline in the performance of LEDs 204, for example.

In some embodiments, CMOS camera module 104 may have the ability to capture images at multiple exposure times. In these embodiments, processor 710 may execute exposure control module 746 to automatically select the captured image with the optimum exposure time which does not cause detector saturation. Exposure control module 746 may contain a decision tree algorithm to automatically select the optimum exposure time, allowing the dynamic range of optical read system 100 to be extended over previously used systems without compromising analytical sensitivity or adding additional cost.

Exposure control module 746 may particularly be used for applications where it is required to quantitatively measure an analyte target from a low level of analyte concentration to a high level. In such applications, previously used systems are often tuned to have the optimum response at low levels of analyte concentration. The reason for this is that high analytical sensitivity is usually the primary objective. However, this frequently results in detectors in such previously used systems saturating at high levels of analyte concentration. Accordingly, this means that such previously known systems are unable to quantitate the analyte concentration over a full range, and the dynamic range of such systems is compromised.

Colour decoding module 748 may be executed by processor 710 to provides a further means of filtering fluorescent emitted light into discrete wavelength intervals, aside from the physical filtration provided by excitation filter 206. Colour decoding module 748 may be of assistance in delineating and thereby enhancing desired fluorescent emission of an analyte from unwanted fluorescent emission from background artefacts such as from diagnostic cartridges 105, for example.

In order to do this, Red-Green-Blue image (RGB) files captures by CMOS camera module 104 may be de-coded by colour decoding module 748 of firmware 740 into an image stack comprising three independent images from each of the pixels in the CMOS array for the Red, Green. and Blue channels respectively. For a fluorophore such as Europium (which emits an orange colour primarily at 615 nm), in some instances it is desirable to discard the results from the Green and the Blue channel (since these may contain remnants of the undesired fluorescent excitation signal which were not blocked by the excitation filter), and to process the fluorescent emitted response solely on the Red channel. For other fluorophores, for example fluorescein or FAM (which emits a green colour at 515 nm), it is desirable to discard the Red and the Blue channels, and process the results on the Green channel. Although this image processing approach works best in combination with excitation filter 206, in some assay applications where high sensitivity is not required, using a colour decoding module 748 as described enables excitation filter 206 to be omitted from system 100.

Firmware 740 may further have an analyte detection module 749, for processing an image captured by CMOS camera module 104 in order to determine whether an analyte target is present in the image or not, and in some embodiments to quantitatively determine the amount of such analyte present. Processor 710 executing analyte detection module 749 may be caused to analyse the measured intensity of fluorescent excitation light in an image received from CMOS camera module 104 with known fluorescent excitation light values stored in memory 730 that correspond to the presence of an analyte target. In some embodiments, processor 710 may further determine a quantity of the target analyte based on an intensity of the light values.

Figure 8:
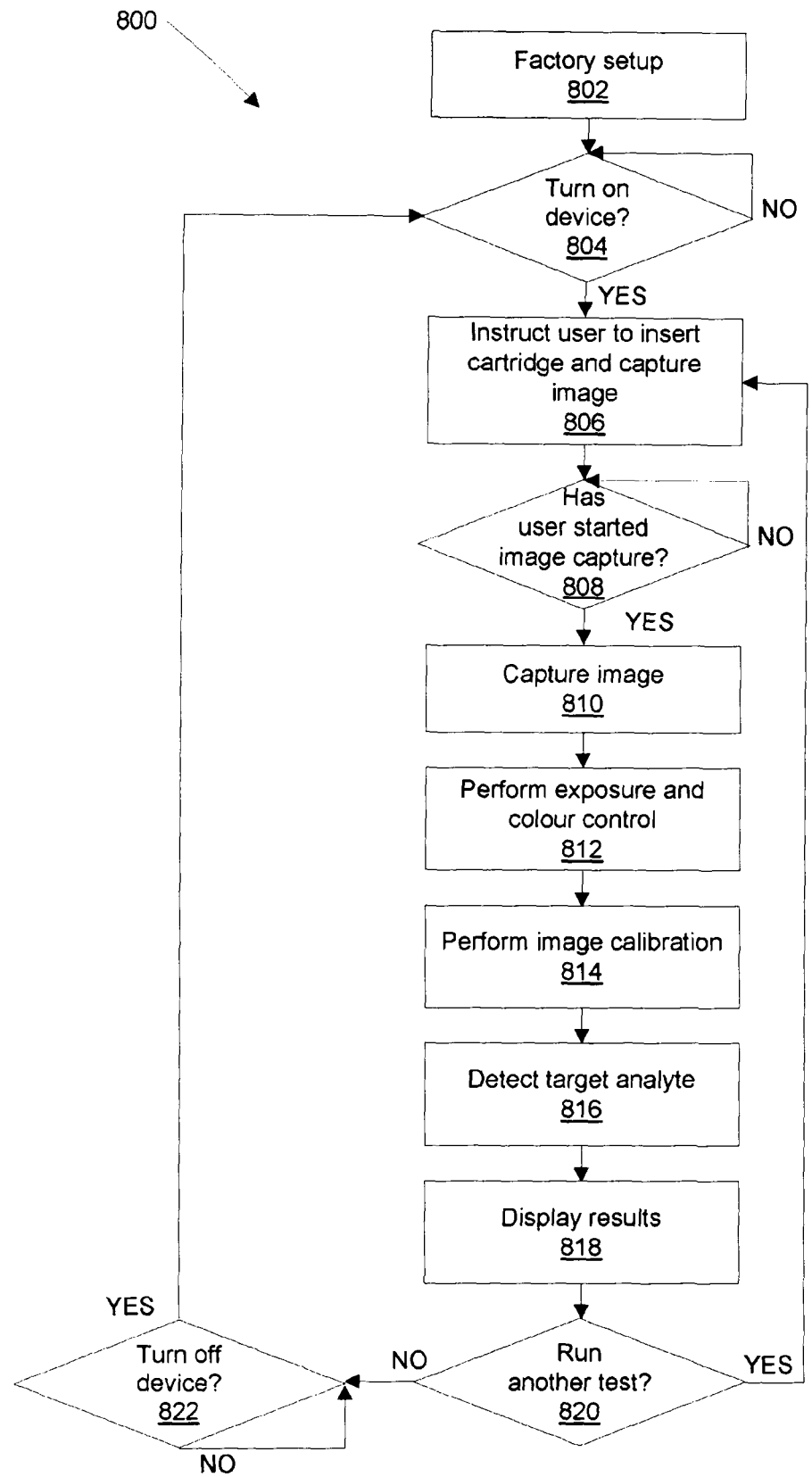
FIG. 8 is a flow diagram showing a method of use of the system of FIG. 1.

FIG. 8 shows a flow diagram 800 showing an example method of performing a test using system 100. At step 802, a factory setup of system 100 is performed, which may include using CMOS camera module 104 to take a calibration image. Processor 710 may execute brightness compensation module 742 in order to use the calibration image to fill illumination look-up table 744 with brightness compensation data as described above with reference to FIG. 7. Factory setup step 802 may be performed prior to use of system 100, and may be performed only once for each system 100. In some embodiments, system 100 may allow factory setup step 802 to be performed multiple times, based on input from a user.

After factory setup step 802 is performed, system 100 waits at step 804 to be turned on. Once system 100 is turned on, which may be performed by plugging system 100 into a power supply, and toggling a "power on" switch or button, for example, system 100 may instruct a user to insert diagnostic cartridge 105 at step 806. The instructions may be displayed on display 760 of system 100 in some embodiments. In some embodiments, they may be communicated through a speaker or other output means. The user may also be instructed to begin image capture once cartridge 105 is in place.

At step 808, system 100 may wait for the user to begin image capture, which may be done by pressing an image capture button, for example. Once the user begins image capture, system 100 captures an image at step 810, using CMOS camera module 104. This step may include powering on LEDs 204 in order to illuminate viewing window 110 prior to capturing the image.

At step 812, system 100 may perform exposure and colour control steps, using exposure control module 746 and colour decoding module 748, as described above with reference to FIG. 7. System 100 may subsequently perform image calibration at step 814 using brightness compensation module 742. This may include scaling the captured image using values from LUT 744, as well as by scaling the image intensity based on calibration markers, as explained above with reference to FIG. 7.

Once calibration is completed, the captured and calibrated image may be passed to analyte detection module 749 to detect the presence and/or quantity of analytes in the sample being processed, at step 816. The results of the analysis may be displayed on display 760 at step 818, or communicated via the output module 720 to an external processing device 750.

The user may then be prompted at step 820 to run another test. If they choose to run another test, the method may be repeated from step 806. Alternatively, the user may be prompted to turn off the device at step 822. If the device is turned off, the method returns to step 804.

The embodiments described above provide a simplified optical read system 100, primarily for fluorescent lateral flow tests, which addresses the problems of cost and excessive complexity of previously used fluorescent readers. Although described embodiments are primarily directed towards reading lateral flow assays, and are described in relation to such assays, it will be appreciated by the person skilled in the art that the subject of the invention may be applied more broadly to other in-vitro diagnostic application (for example, reading a fluorescent response from molecular diagnostic assays where the amplified target is present in a well of a microfluidic device, or reading the results of on-chip or on-slide hybridisation assays as microarrays, or reading the results of such assays in multi-well plates).

Although selected aspects have been illustrated and described in detail, it will be understood that various substitutions and alterations may be made therein without departing from the spirit and scope of the present invention.

The invention claimed is:

1. A system for reading diagnostic assays for in-vitro diagnostic applications, the system comprising:
   a receiving member that receives a diagnostic assay cartridge carrying a diagnostic assay;
   at least one excitation module that illuminates the diagnostic assay, when the diagnostic assay cartridge is placed in the receiving member;
   a camera module that captures an image of the illuminated diagnostic assay placed in the receiving member;
   a processor; and
   memory storing firmware accessible to the processor;
   wherein when the processor executes the firmware, the processor is caused to receive the captured image from the camera module, adjust the intensity of the image to emulate a uniform field of illumination over the diagnostic cartridge based on an illumination look-up table, and based on the captured image, determine an amount of a target analyte that was present in the diagnostic assay.

2. The system of claim 1, wherein the diagnostic assay cartridge is a fluorescent-labelled diagnostic assay cartridge carrying a fluorescent-labelled diagnostic assay, and the calibration marker is a fluorescent calibration marker.

3. The system of claim 1, further comprising at least one calibration marker located in the field of view of the camera module, for evaluating the expected response from the at least one excitation module.

4. The system of claim 3, wherein the brightness compensation module is configured to adjust the intensity of the captured image based an evaluation of the expected response from the at least one excitation module determined based on the at least one calibration marker.

5. The system of claim 3, wherein the calibration marker is located on the receiving member.

6. The system of claim 1, wherein the processor is further configured to compare the amount of the target analyte detected with a predetermined threshold to determine whether or not a threshold amount of the analyte was present in the diagnostic assay.

7. The system of claim 1, wherein the firmware includes an exposure control module for adjusting the exposure of an image captured by the camera module.

8. The system of claim 1, wherein the at least one excitation module, the camera module and the processor are located on an optical read device.

9. The system of claim 1, wherein the at least one excitation module and the camera module are located on an optical read device, and the processor is located on an external device remote from the optical read device.

10. The system of claim 1, wherein the system is in communication with at least one external processing device.

11. The system of claim 1, wherein the camera module comprises a CMOS camera module.

12. The system of claim 1, wherein the parts of the system are configured to be substantially fixed relative to one another while the camera module captures an image of the diagnostic assay.

13. The system of claim 1, wherein the at least one excitation module comprises at least two excitation modules.

14. The system of claim 13, wherein the excitation modules are each counter-disposed at an oblique angle to the receiving member.

15. The system of claim 13, wherein each of the at least two excitation modules are configured to operate contemporaneously to illuminate the diagnostic assay, when the diagnostic assay is placed in the receiving member.

16. The system of claim 1, wherein the illumination compensation look-up table is generated based on a calibration image captured by the camera module, and is stored in the firmware.

17. The system of claim 1, wherein the firmware includes a colour decoding module for separating an image captured by the camera module into colour channels.

18. The system of claim 1, wherein each excitation module comprises at least one LED.

19. The system of claim 1, wherein each excitation module comprises at least one light shaping element to produce a near-collimated beam of excitation light.

20. The system of claim 1, wherein each excitation module comprises at least one optical filter.

* * * * *